(12) United States Patent
Klima (10) Patent No.: US 9,039,676 B2
(45) Date of Patent: May 26, 2015

(54) APPARATUS AND METHODS FOR CATHETER STEERABILITY

(75) Inventor: Daniel J. Klima, Andover, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 595 days.

(21) Appl. No.: 12/796,200

(22) Filed: Jun. 8, 2010

(65) Prior Publication Data

US 2010/0318067 A1 Dec. 16, 2010

Related U.S. Application Data (60) Provisional application No. 61/186,087, filed on Jun. 11, 2009.

(51) Int. Cl.
*A61M 25/00* (2006.01)
*A61M 25/01* (2006.01)

(52) U.S. Cl.
CPC ....... *A61M 25/0138* (2013.01); *A61M 25/0147* (2013.01)

(58) Field of Classification Search
USPC .......................... 600/139–143; 604/524–530
See application file for complete search history.

(56) References Cited

U.S. PATENT DOCUMENTS

| | | | | |
|---|---|---|---|---|
| 4,911,148 | A * | 3/1990 | Sosnowski et al. | 600/136 |
| 5,329,923 | A * | 7/1994 | Lundquist | 600/373 |
| 5,477,856 | A * | 12/1995 | Lundquist | 600/373 |
| 6,491,626 | B1 * | 12/2002 | Stone et al. | 600/141 |
| 6,585,718 | B2 * | 7/2003 | Hayzelden et al. | 604/523 |
| 6,749,560 | B1 * | 6/2004 | Konstorum et al. | 600/143 |
| 6,776,765 | B2 * | 8/2004 | Soukup et al. | 600/585 |
| 6,907,298 | B2 * | 6/2005 | Smits et al. | 607/125 |
| 2002/0082585 | A1 * | 6/2002 | Carroll et al. | 604/528 |
| 2004/0199051 | A1 * | 10/2004 | Weisel | 600/141 |
| 2004/0225186 | A1 * | 11/2004 | Horne et al. | 600/139 |
| 2005/0070844 | A1 * | 3/2005 | Chow et al. | 604/95.04 |
| 2005/0096590 | A1 * | 5/2005 | Gullickson et al. | 604/95.04 |
| 2005/0131343 | A1 * | 6/2005 | Abrams et al. | 604/95.04 |
| 2006/0004346 | A1 * | 1/2006 | Begg | 604/525 |
| 2006/0041188 | A1 * | 2/2006 | Dirusso et al. | 600/146 |
| 2006/0241564 | A1 * | 10/2006 | Corcoran et al. | 604/523 |
| 2006/0264904 | A1 * | 11/2006 | Kerby et al. | 604/523 |
| 2007/0005018 | A1 * | 1/2007 | Tekbuchava | 604/164.01 |
| 2007/0260225 | A1 * | 11/2007 | Sakakine et al. | 604/528 |
| 2008/0097398 | A1 * | 4/2008 | Mitelberg et al. | 604/525 |
| 2008/0172037 | A1 * | 7/2008 | Huang et al. | 604/526 |
| 2008/0188928 | A1 * | 8/2008 | Salahieh et al. | 623/2.11 |
| 2009/0177040 | A1 * | 7/2009 | Lyons et al. | 600/141 |
| 2009/0192495 | A1 * | 7/2009 | Ostrovsky et al. | 604/528 |
| 2010/0057037 | A1 * | 3/2010 | Webler | 604/500 |
| 2010/0069882 | A1 * | 3/2010 | Jennings et al. | 604/525 |

\* cited by examiner

*Primary Examiner* — Nicolas Lucchesi
*Assistant Examiner* — Gerald Landry, II
(74) *Attorney, Agent, or Firm* — Holland & Hart (57) ABSTRACT

A catheter assembly having first and second shaft members that provide stearability for the catheter assembly. The first shaft member has a plurality of longitudinally spaced apart first ring members that are interconnected with a longitudinally extended first spine member. The second shaft member is positioned within the first shaft member and is connected to a distal end portion of the first shaft member. The second shaft member has a plurality of longitudinally spaced apart second ring members that are interconnected with a longitudinally extending second spine member. Alternatively, the second shaft member includes a plurality of protrusions extending radially outward from the longitudinally extending second spine member. The second shaft member is operable to move at least portions of the first ring members longitudinally relative to each other to bend the first shaft member.

23 Claims, 5 Drawing Sheets

APPARATUS AND METHODS FOR CATHETER STEERABILITY

CROSS-REFERENCE TO RELATED APPLICATION

This application claims the benefit of U.S. Provisional Patent Application No. 61/186,087, filed 11 Jun. 2009, which is hereby incorporated by reference herein in its entirety.

TECHNICAL FIELD

The present disclosure relates generally to catheter devices, and more particularly relates to steerable catheters and catheter steering mechanisms and methods.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Endovascular therapy has been used to treat different conditions. Such treatments include control of internal bleeding, occlusion of blood supply to tumors, and occlusion of aneurysm. Often the target site is difficult to reach. Catheters are increasingly becoming components of endovascular therapies because of their ability to access remote regions of the human body and deliver diagnostic or therapeutic agents. Catheters are often introduced into large arteries, such as those in the groin or in the neck, and then passed through narrowing regions of the arterial system until reaching the selected target site. Catheters are often stiffer at their proximal end to allow the pushing and manipulation of the catheter as it progresses through the body, but sufficiently flexible at the distal end to allow passage of the catheter tip through the body's blood vessels.

In order to maneuver around turns and bends in the vasculature, an operator may observe the catheter fluoroscopically and selectively deflect the tip and rotate the proximal end of the catheter shaft. The ability to control the precise position of the distal end of the catheter depends on the catheter's ability to transmit forces exerted at the proximal end to the distal end. Without proper rotational and longitudinal force transmission, the operator may be unable to control precisely the catheter tip and, consequently, the operating procedure may be delayed or less effectively performed.

SUMMARY

One aspect of the present disclosure relates to a catheter assembly that includes first and second shaft members. The first shaft member has a plurality of longitudinally spaced apart first ring members that are interconnected with a longitudinally extended first spine member. The second shaft member is positioned within the first shaft member and is connected to a distal end portion of the first shaft member. The second shaft member has a plurality of longitudinally spaced apart second ring members that are interconnected with a longitudinally extending second spine member. Alternatively, the second shaft member includes a plurality of protrusions extending radially outward from the longitudinally extending second spine member. The second shaft member is operable to move at least portions of the first ring members longitudinally relative to each other to bend the first shaft member.

The first ring members may be aligned with the second ring members. The protrusions may extend radially outward into a space defined between adjacent first ring members. The second shaft member may be operable to rotate relative to the first shaft member to contact the protrusions with the first ring members to space apart the first ring members. The catheter assembly may include a longitudinal axis, and the first and second shaft members may be coaxial with the longitudinal axis.

The second shaft member may be configured to bend in a first direction upon application of a distally directed longitudinal force that causes the first shaft member to bend in the first direction. Bending the second shaft member in the first direction spaces apart at least portions of the second ring members, and bending the first shaft member in the first direction moves at least portions of the first ring members closer together. Applying a proximally directed longitudinal force to the second shaft member bends the second shaft member in a second direction causing the first shaft member to bend in the second direction. Bending the second shaft member in the second direction moves at least portions of the second ring members closer together, and bending the first shaft member in the first direction spaces apart at least portions of the first ring members. The first shaft member may be configured as an integral single piece, and the second shaft member may be configured as an integral single piece. A spacing between adjacent first ring members may vary around a circumference of the first shaft member when the first shaft member is in a rest state.

Another aspect of the present disclosure is directed to a method of bending a distal end portion of the catheter assembly. The method may include providing the distal end portion of the catheter assembly with a first shaft portion and a second shaft portion. The second shaft portion extends through a lumen defined by the first shaft portion, and the first shaft portion includes a plurality of longitudinally spaced apart first openings. The second shaft portion may include one of a plurality of longitudinally spaced apart second openings or a plurality of protrusions that extend radially outward into the first openings. The method may also include operating the second shaft portion to bend the first shaft portion when the first shaft portion is in a rest state.

Operating the second shaft portion includes axially advancing or retracting the second shaft portion to change a size or shape of the second openings and a size or shape of the first openings. Operating the second shaft portion may include rotating the second shaft portion to move the protrusions within the first opening, wherein the first openings have a variable width around a circumference of the first shaft portion.

Another aspect of the present disclosure is directed to a catheter portion that includes a body portion and a steering member. The body portion has a bendable section and defines a lumen. A series of longitudinally spaced apart first openings are defined in the bendable section. The steering member extends through the lumen of the body portion and is connected at a distal end thereof to the body portion. The steering member includes a series of longitudinally spaced apart second openings. Application of an axial force to the steering member bends the steering member and bends the bendable portion of the body portion.

The body portion may be coaxial with the steering member. The first openings may be arranged facing in a direction opposite a direction in which the second openings are facing. The second openings may be configured to close in a longitudinal direction and the first openings may be configured to enlarge in the longitudinal direction upon application of a distally directed axial force to the steering member. The second openings may be configured to enlarge in a longitudinal direction and the first openings may be configured to close in a longitudinal direction upon application of a proximally directed axial force to the steering member. The first openings may extend around at least half of a circumference of the body portion, and the second openings may extend around at least half of a circumference of the steering member.

A further aspect of the present disclosure is directed to a catheter portion that includes a body portion and a steering member. The body portion includes a bendable section and defines a lumen. A series of longitudinally spaced apart first openings are defined in the bendable section. The steering member extends through the lumen of the body portion and is connected at distal end thereof to the body portion. The steering member includes a series of radially extending, longitudinally spaced apart protrusions that extend into the first openings. The steering member is configured to bend the bendable portion of the body portion upon application of a rotational force to the steering member.

Protrusions of the steering member may be configured to widen the first openings in the longitudinal direction upon application of a rotational force to the steering member. The first openings may have a variable width around a circumference of the body portion when the body portion is in a rest state. The first openings may extend only partially around a circumference of the body portion.

Additional advantages and novel features will be set forth in the description which follows or may be learned by those skilled in the art through reading these materials or practicing the examples disclosed herein. The advantages of the invention may be achieved through the limitations recited in the attached claims.

BRIEF DESCRIPTION OF THE DRAWINGS

The accompanying drawings illustrate various embodiments of the present disclosure and are a part of the specification. The illustrated embodiments are merely examples and do not limit the scope of the invention.

Throughout the drawings, identical reference numbers designate similar, but not necessarily identical, elements.

DETAILED DESCRIPTION

The present disclosure is directed in part to a steerable, medical device in the form of, for example, a steerable catheter assembly. A catheter assembly is adapted and configured for gaining access to and/or pointing within a body cavity. The catheter assembly may be used with other devices such as, for example, fiber optics, irrigation, aspiration, dilation catheters, biopsy or other tissue removal apparatus, and the like, that are inserted through or advanced over the steerable catheter assembly. The disclosed catheter assemblies and related methods are particularly well suited for use in blood vessels and other body lumens such as vein graphs, carotid arteries, coronary arteries, renal arteries, cerebrals, iliacs, femorals, and peripheral arteries. It is contemplated that the catheter assemblies and methods disclosed herein may be adapted for use in other areas of the body, such as various body organs. Medical applications of particular interest include gastroenterology, urology, gynecology, ear, nose and throat applications, orthopedics (arteroscopy), angioscopes, neurology and cardiology.

In general, the steerable catheter assembly of the present disclosure is applicable in any environment in which it is desirable to controllably deflect the distal tip of a working implement. Alternatively, the steerable aspects disclosed herein may be incorporated into or be appendages to non-steerable devices, as would be apparent to those of skill in the art.

As used in this specification and the appended claims, the term "engage" and "engagable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "shaft" is an elongated device that may or may not define a lumen or other passageway. A "lumen" refers to any open space or cavity in a bodily organ, especially in a blood vessel. The words "including" and "having," as used in the specification, including the claims, have the same meaning as the word "comprising."

Figures 1, 2:
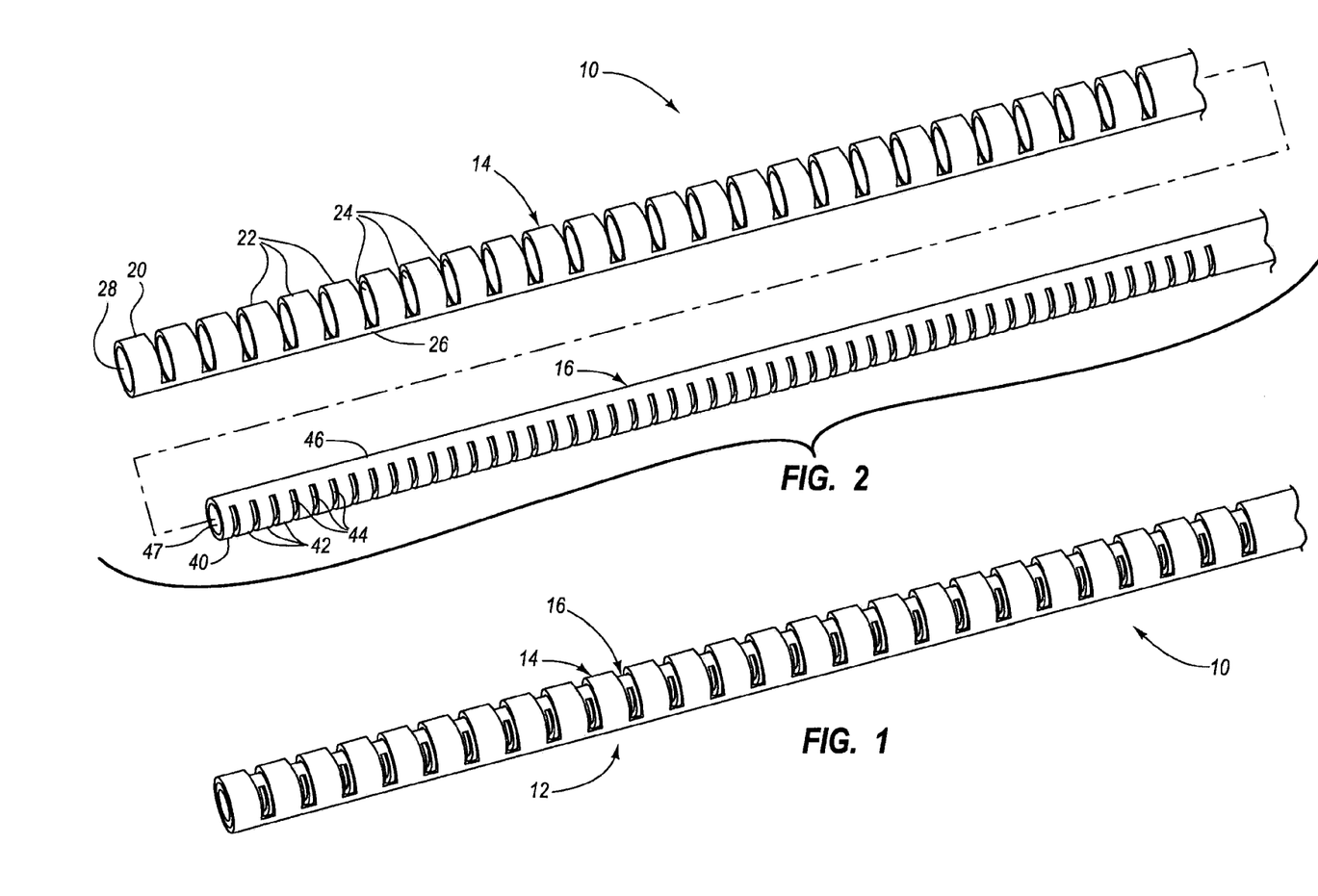
FIG. 1 is a perspective view of a distal portion of an example catheter assembly in accordance with the present disclosure.
FIG. 2 is an exploded perspective view of the catheter assembly of FIG. 1.
Figure 3:
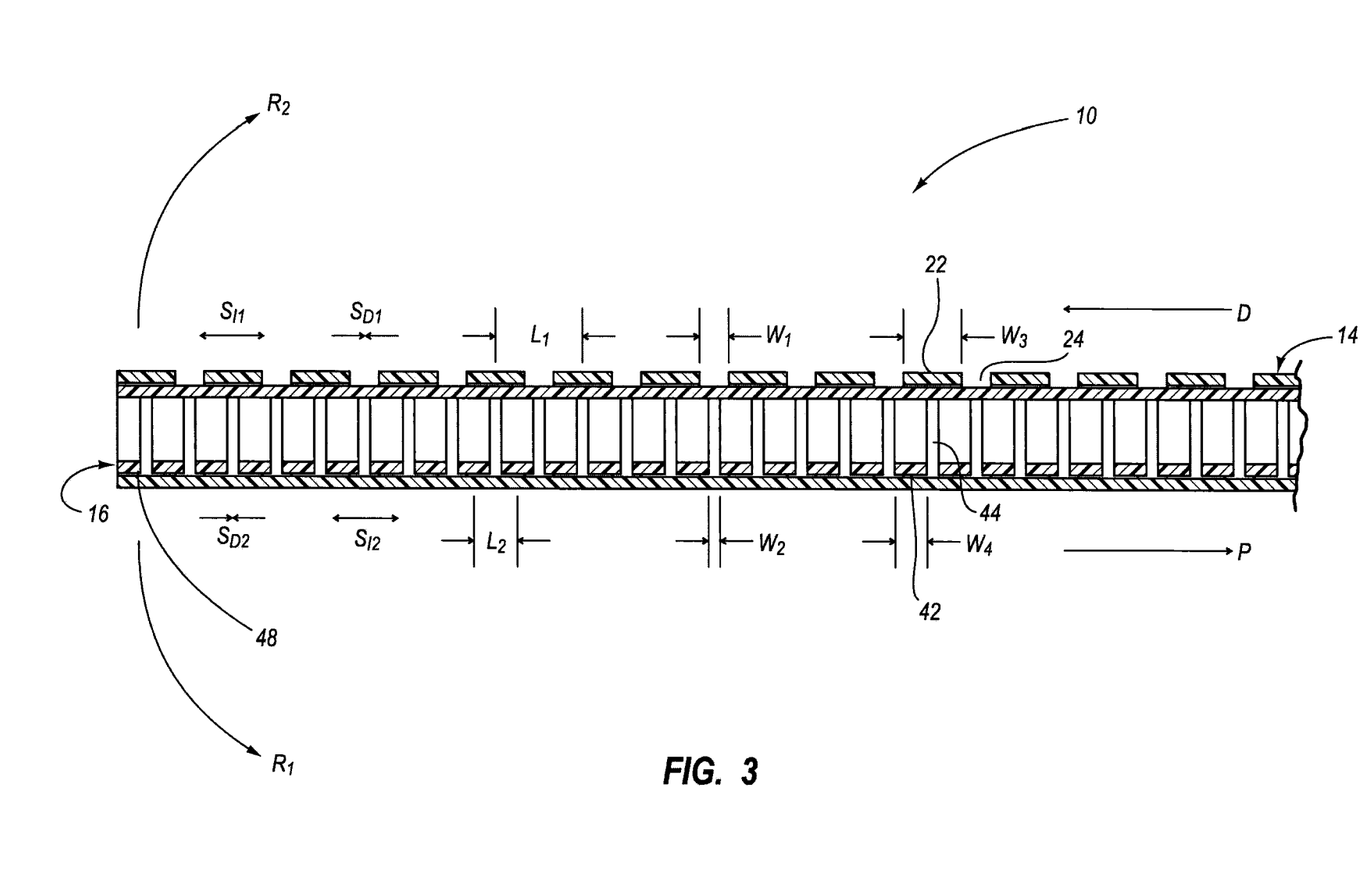
FIG. 3 is a cross-sectional view of the catheter assembly of FIG. 1.

Referring first to FIGS. 1-3, an example catheter assembly 10 is shown and described. The catheter assembly 10 includes a distal portion 12 that is prominently displayed in the figures. The catheter assembly 10 may include features located proximal of the distal portion 12 that are accessible or operable outside of the patient while the distal portion 12 is positioned within a patient.

The catheter assembly 10 includes a body portion 14 (also referred to herein as a first shaft portion), and a steering portion 16 (also referred to herein as a second shaft portion). The body portion 14 includes a distal end 20, a plurality of rings 22 that are longitudinally spaced apart along a length of the body portion 14, and a plurality of openings 24 defined between adjacent rings 22. At least FIG. 1 shows a single one of the openings 24 being arranged at any given longitudinal position along a length of the body portion 14. The rings 22 are interconnected with a spine 26 (also referred to herein as a longitudinal support member). The spine 26 typically extends along a common side of each of the rings 22. A body portion 14 defines a lumen 28 that extends along a length of the body portion 14 and is defined in part by each of the rings 22.

The openings 24 define an opening width $W_1$ (see FIG. 3). The opening width $W_1$ may vary as the rings 22 move relative to each other in the longitudinal direction. Typically, the opening width $W_1$ is relatively constant between all adjacent rings 22 when the body portion 14 is in a rest state. The rest state for the body portion 14 may be defined as a state in which no external axial, rotational, or transverse forces are applied to the body portion 14.

The rings 22 are typically spaced apart a length distance $L_1$, which is also referred to herein as a longitudinal spacing $L_1$. FIG. 3 illustrates a longitudinal spacing $L_1$ being measured between a longitudinal center point of adjacent rings 22. Typically, the longitudinal spacing $L_1$ is generally constant between all adjacent rings along the length of the body portion when the body portion 14 is in a rest state.

It may be possible to have different openings widths $W_1$ between some of the rings 22 when the body portion 14 is in a rest state. An increased opening width $W_1$ may provide for additional longitudinal movement of adjacent rings 22 towards each other to provide increased angle of bending in the body portion 14. Further, the longitudinal spacing $L_1$ (independent of the opening width $W_1$) may have different dimensions for different ring members along the length of the body portion 14. Any one of the ring members 22 may have a ring width $W_3$ (see FIG. 3) that is different in size and width than an adjacent ring, which may alter the longitudinal spacing $L_1$.

When the body portion 14 is bent in a direction $R_1$, the spacing between adjacent rings (i.e., the width $W_1$) increases to create a spacing increase $S_{I1}$. When the body portion 14 is bent in the rotation direction $R_2$, the spacing between adjacent rings decreases causing a spacing decrease $S_{D1}$. The width $W_1$, at least in part, controls a maximum amount of bend in the direction $R_2$ that is possible for the body portion 14. As the width $W_1$ decreases to zero by bending in the direction $R_2$, the adjacent rings 22 eventually contact each other to resist further bending in the direction $R_2$.

The construction of the spine 26 may also influence the amount of bending in the directions $R_1$ and $R_2$. The material properties, such as elasticity, flexibility and/or stiffness of the spine 26, as well as the structure (i.e., thickness, width and contour) of the spine 26 may all influence the amount of bend in the directions $R_1$ and $R_2$.

The steering portion 16 includes a distal end 40, and a plurality of longitudinally spaced apart rings 42 that are interconnected with a spine 46 (also referred to herein as a longitudinal support member). The spine 46 typically extends along a common side of the rings 42. A plurality of openings 44 are defined between adjacent rings 42. The steering portion 16 may also define a lumen 47 that extends along a length of the steering portion 16 and is defined in part by at least some of the rings 42.

The openings 44 define an opening width $W_2$ (see FIG. 3). The opening width $W_2$ may vary as the rings 42 move relative to each other in the longitudinal direction. In at least one arrangement, the opening width $W_2$ is relatively constant between all adjacent rings 42 when the steering portion 16 is in a rest state. The rest state for the steering portion 16 may be defined as a state in which no external axial, rotational, or transverse forces are applied to the steering portion 16.

The rings 22 are typically spaced apart a distance $L_2$, which is also referred to herein as a longitudinal spacing $L_2$. FIG. 3 illustrates a longitudinal spacing $L_2$ measured between a longitudinal center point of adjacent rings 42. In at least one arrangement, the longitudinal spacing $L_2$ is generally constant between all adjacent rings along the length of the steering portion 16 when the steering portion 16 is in a rest state.

It may be possible to have different openings widths $W_2$ between some of the rings 42 when the steering portion 16 is in a rest state. An increased opening width $W_2$ may provide for additional longitudinal movement of adjacent rings 42 towards each other to provide an increased angle of bending in the steering portion 16 when the steering portion 16 is bent in the direction $R_2$ shown in FIG. 3. The longitudinal spacing $L_2$ may be independent of the opening width $W_2$ and may have different dimensions for different ring members along the length of the steering portion 16. For example, any one of the ring 42 may have a ring width $W_4$ (see FIG. 3) that is different in size and width than an adjacent ring, which may alter the longitudinal spacing $L_2$.

When the steering portion 16 is bent in direction $R_1$, the spacing between adjacent rings (i.e., the width $W_2$) decreases to create a spacing decrease $S_{D2}$. When the steering portion 16 is bent in the rotation direction $R_2$, the spacing between adjacent rings increases causing a spacing increase $S_{I2}$. The width $W_2$, at least in part, controls a maximum amount of bend in direction $R_1$ that is possible for the steering portion 16. As the width $W_2$ decreases to zero by bending in the direction $R_1$, the adjacent rings 42 eventually contact each other to resist further bending in the direction $R_1$.

The construction of the spine 46 may also influence the amount of bending in the directions $R_1$ and $R_2$. The material properties (e.g., elasticity, flexibility and/or stiffness of the spine 46, as well as the structure (e.g., thickness, width and contour) of the spine 46 may influence the amount of bend in the directions $R_1$ and $R_2$.

The steering portion 16 is inserted through the lumen 28 of the body portion 14. Typically, the steering portion 16 is connected to the body portion 14 at a location along the length of the body portion 14. In one example, the distal end 40 of the steering portion 16 is connected to the distal end 20 of the body portion 14 at a connection point 48 (see FIG. 3). In other arrangements, the steering portion 16 may be connected at other locations along the length of the body portion 14. Alternatively, steering portion 16 may be connected to the body portion 14 at any location along the length of the steering portion 16 such as, for example, at a location spaced proximal of the distal end 40. Furthermore, the distal end 40 of the steering portion 16 may be positioned proximal of the distal end 20 of the body portion 14. In other arrangements, the distal end 40 of the steering portion 16 may be positioned distal of the distal end 20 of the body portion 14. Many other relative axial positions are possible for the body portion 14 and steering portion 16 when the catheter assembly 10 is assembled.

The connection between the body portion 14 and steering portion 16 may provide that any bending that occurs in the body portion 14 also occurs in the same bend direction in the steering portion 16, and vice versa. Typically, applying an axial directed force in either the distal or proximal direction to either one of the body portion 14 and steering portion 16 while maintaining the other of the body portion 14 and steering portion 16 in a fixed axial position will cause bending in one of the directions $R_1$ and $R_2$.

In one example, the body portion 14 is retained in a fixed axial position and an axial force is applied to the steering portion 16 in the proximal direction. Application of a proximally directed axial force to the steering portion 16 causes a spacing increase $S_{I2}$ between adjacent rings 42 of the steering portion 16, thereby bending the steering portion 16 in the direction $R_2$. Bending the steering portion 16 in the direction $R_2$ causes the body portion 14 to also bend in the direction $R_2$ thereby creating a spacing decrease $S_{D1}$ between adjacent rings 22 and the body portion 14.

Application of a distally directed axial force to the steering portion 16 while maintaining the body portion 14 in a fixed axial position creates a spacing decrease $S_{D2}$ between adjacent rings 42 of the steering portion 16 that causes the steering portion 16 to bend in a direction $R_1$. Bending the steering portion 16 in the direction $R_1$ causes the body portion 14 to also bend in the direction $R_1$, thereby creating a spacing increase $S_{I1}$ between adjacent rings 22 of the body portion 14.

The catheter assembly 10 may also be operable to provide bending in the directions $R_1$ and $R_2$ by applying axial directed forces to the body portion 14 while maintaining the steering portion 16 in a fixed axial position. For example, applying a distally directed axial force to the body portion 14 while maintaining the steering portion 16 in a fixed axial position creates a spacing decrease $S_{D1}$ between adjacent rings 22 to provide bending in the direction $R_2$. Bending the body portion 14 in the direction $R_2$ causes the steering portion 16 to also bend in the direction $R_2$, thereby creating a spacing increase $S_{I2}$ between adjacent rings 42. Likewise, applying a proximally directed axial force to the body portion 14 while maintaining the steering portion 16 in a fixed axial position creates a spacing increase $S_{I1}$ between adjacent rings 22 to bend the body portion 14 in the direction $R_1$. Bending the body portion 14 in the direction $R_1$ causes the steering portion 16 to also bend in the direction $R_1$, thereby creating a spacing decrease $S_{D2}$ between adjacent rings 42.

Figure 4:
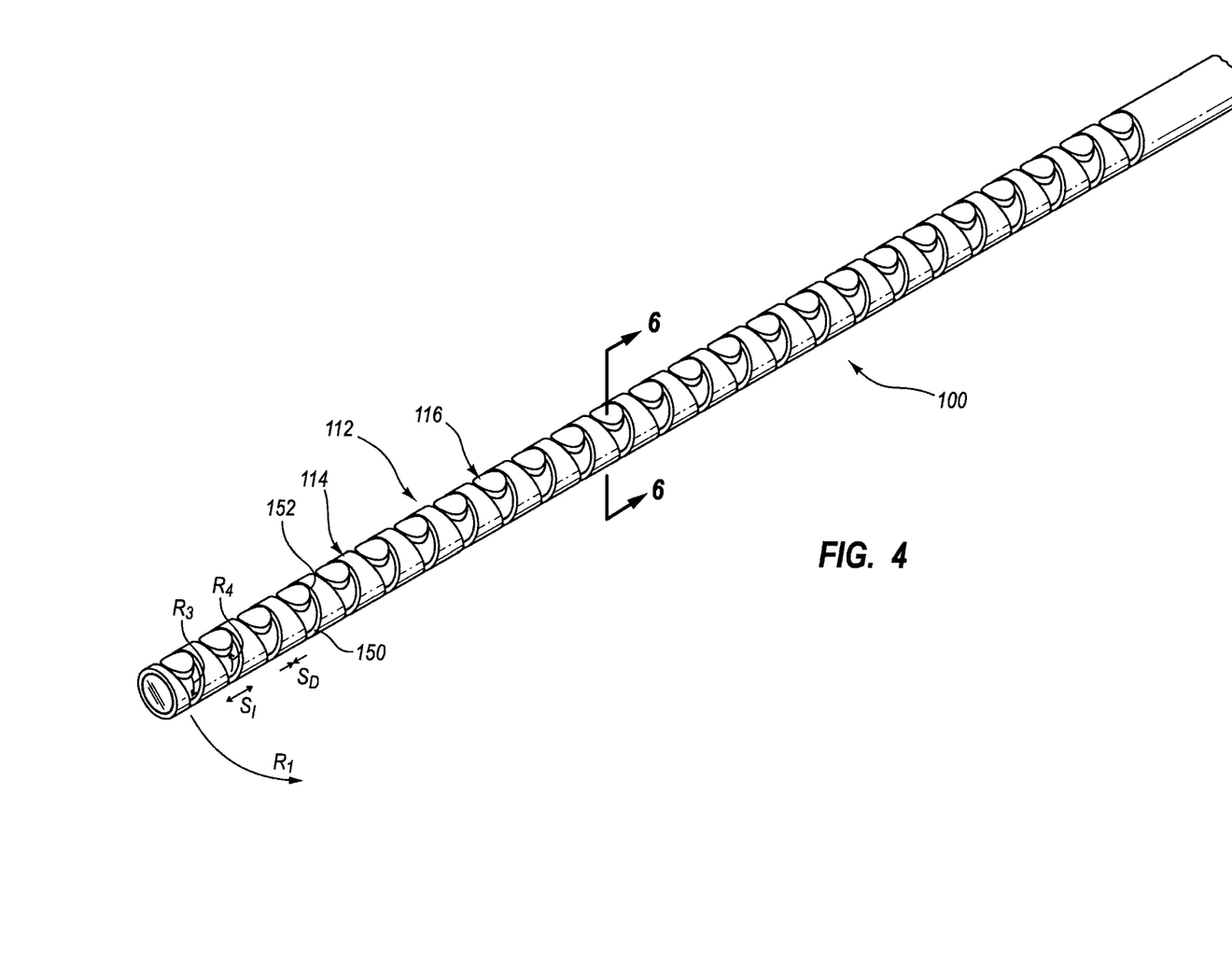
FIG. 4 is a perspective view of a distal end portion of another example catheter assembly in accordance with the present disclosure.
Figure 5:
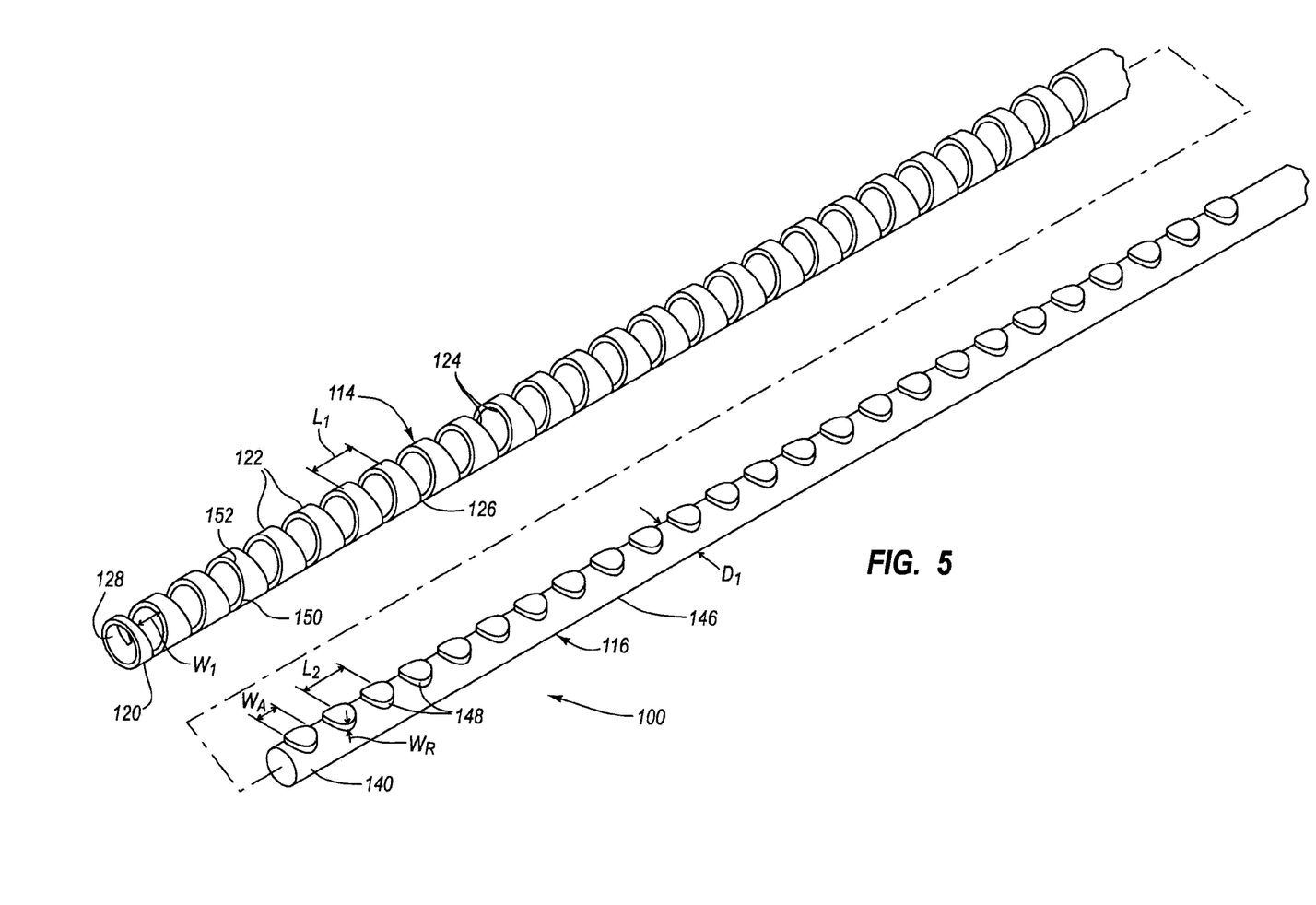
FIG. 5 is an exploded perspective view of the catheter assembly of FIG. 4.
Figure 6:
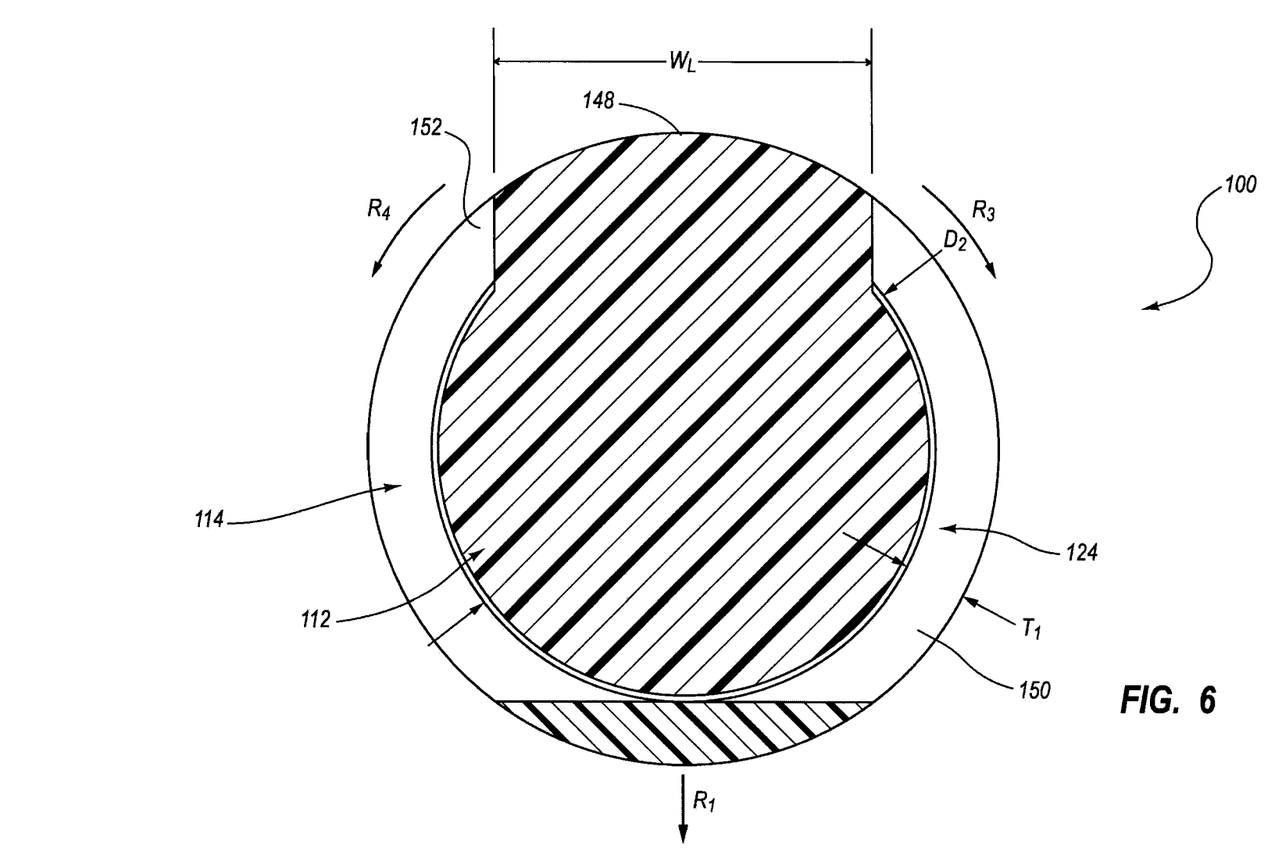
FIG. 6 is a cross-sectional view of the catheter assembly of FIG. 4.

Referring now to FIGS. 4-6, another example catheter assembly 100 is shown and described. The catheter assembly 100 includes a distal end portion 112. The catheter assembly 100 includes a body portion 114 (also referred to herein as a first shaft portion), and a steering portion 116 (also referred to herein as a second shaft portion) positioned at the distal end portion 112. The body portion 114 includes a distal end 120, a plurality of rings 122 longitudinally spaced apart along a length of the body portion 114, and a plurality of openings 124 defined between adjacent rings 122. The rings 122 are interconnected with a spine 126 (also referred to herein as a longitudinal support member) that typically extends along a common side of each of the rings 122. A body portion 114 defines a lumen 128 that extends along a length of the body portion 114 and is defined in part by each of the rings 122.

The openings 124 define an opening width $W_1$ (see FIG. 5). The opening width $W_1$ may vary as the rings 122 move relative to each other in the longitudinal direction. The opening width $W_1$ may be variable between adjacent rings 122 when the body portion 114 is in a rest state. The rest state for the body portion 114 may be defined as a state in which no external axial, rotational, or transverse forces are applied to the body portion 114.

The rings 122 are typically spaced apart a distance $L_1$, which is also referred to herein as a longitudinal spacing $L_1$. FIG. 5 illustrates a longitudinal spacing $L_1$ being measured between a longitudinal center point of adjacent rings 122. Typically, the longitudinal spacing $L_1$ is generally constant between all adjacent rings along the length of the body portion when the body portion 114 is in a rest state.

It may be possible to have different openings widths $W_1$ between some of the rings 122 when the body portion 114 is in a rest state. An increased opening width $W_1$ may provide for additional longitudinal movement of adjacent rings 122 towards each other to provide an increased angle of bending in the body portion 114. For example, when the body portion 114 is bent in a direction $R_2$ shown in FIG. 4, the longitudinal spacing $L_1$ may have different dimensions for different ring members along the length of the body portion 114. Further, any one of the rings 122 may have a ring width $W_3$ (see FIG. 5) that is different in size and width than an adjacent ring, which may alter the longitudinal spacing $L_1$.

When the body portion 114 is bent in a direction $R_1$, the spacing between adjacent rings (i.e., the width $W_1$) increases to create a spacing increase $S_I$. The width $W_1$, at least in part, controls a maximum amount of bend in the direction $R_1$ that is possible for the body portion 114. As the width $W_1$ decreases, the adjacent rings 122 eventually contact each other to resist further bending.

The construction of the spine 126 may also influence the amount of bending in the directions $R_1$. The material properties (e.g., elasticity, flexibility and/or stiffness) of the spine 126, as well as the structure (e.g., thickness, width and contour) of the spine 126 may influence the amount of bend in the directions $R_1$.

The steering portion 116 includes a distal end 140, a spine 146 (also referred to herein as a longitudinal support member), and a plurality of protrusions 148 positioned along a length of the spine 146. The steering portion 116 is inserted into the lumen 128 of the body portion 114. The protrusions 148 are radially aligned with the openings 124 of the body portion 114. Each of the protrusions 148 has a radial width $W_R$, an axial width $W_A$, and a lateral width $W_L$. The protrusions 148 may have at least some taper in the lateral direction along the lateral width $W_L$ so that the axial width $W_A$ changes in the lateral direction. The radial width $W_R$ is typically sufficient so that protrusion 148 extends at least partially into the openings 124 when the steering portion 116 is positioned within the lumen 128 of the body portion 114.

A diameter $D_1$ of the spine 46 is substantially similar (i.e., within about 90% to 100%) to the diameter $D_2$ of the lumen 128 (see FIGS. 5 and 6). The radial width $W_R$ may be substantially similar to (i.e., within about 80% to 120%) a thickness $T_1$ of the body portion 114 (see FIGS. 5 and 6). In other arrangements, the diameter $D_1$ may be substantially less than the diameter $D_2$ and the radial width $W_R$ is substantially greater than the thickness $T_1$ to maintain positioning of the protrusions 148 within the openings 124.

In operation, the steering portion 116 is maintained in a fixed axial position within the lumen 128 of the body portion 114. For example, in one arrangement the distal end 140 of the steering portion 116 is connected to the distal end 120 of the body portion 114 with a retaining device such as, for example, a clip, bearing, or tongue and groove feature that provides rotation of the steering portion 116 relative to the body portion 114 while restricting axial movement of the body portion 114 relative to the steering portion 116.

The protrusions 148 are positioned at least partially within the openings 124. As the steering portion 116 rotates in either the direction $R_3$ or the direction $R_4$ (see FIG. 4), the protrusion 148 moves from a center portion 152 of the openings 124 towards an end portion 150 of the opening 124. The axial width $W_A$ of the protrusions 148 may be greater than the width $W_1$ of the openings 124 towards the end portion 150. The protrusions 148 exert an axial force upon adjacent rings 122 to create a spacing increase $S_I$ between adjacent rings 122 (see FIG. 4). Increasing the spacing between adjacent rings 122 tends to bend the catheter assembly 100 in the rotation direction $R_1$. Rotating the steering portion 116 in the direction $R_4$ to move the protrusions 148 from the end portion 150 of the opening 124 towards the center portion 152 of the opening 124 permits a spacing decrease $S_D$ between adjacent rings 122. Permitting the rings 122 to move back towards each other after being axially spaced apart tends to permit the catheter assembly 100 to rotate in the direction $R_2$ back to a rest state (i.e., a state wherein the catheter assembly 100 is in a generally linear arrangement with no rotational, lateral, or axial forces being applied to the catheter assembly 100).

The construction of protrusions 148 and the openings 124 may be different at various locations along the length of the catheter assembly 100. Varying the size, shape, and orientation of the protrusions 148 or the openings 124 may influence the amount of spacing increase or spacing decrease occurs between adjacent rings 122 at different locations along the length of the catheter assembly 100 as the steering portion 116 is rotated relative to the body portion 114. The size, shape and orientation of the protrusions 148 and openings 124 may change along the length of the body and steering portions 114, 116 to provide different amounts of bending in directions $R_1$, R₂ at various positions along the length of catheter assembly 100. For example, the protrusions 148 and the openings 124 near the distal ends 120, 140 may be configured to provide a greater spacing increase between adjacent rings 122 for a given amount of relative rotation between body and steering portions 114, 116 as compared to the amount of spacing increase provided between adjacent rings 122 at proximal locations along the catheter assembly 100 using the same amount of relative rotation between the body and steering portions 114, 116.

In one example, the protrusions 148 are positioned at slightly offset locations around a circumference of the spine 146 at various locations along the length of the steering portion 116 while the circumferential position of the openings 124 is constant along the length of the body portion 114. This configuration may provide for immediate initiation of bending in the direction R₁ at one location along the length of the catheter assembly 100 upon relative rotation of the body and steering portions 114, 116 followed by delayed bending at other locations along the length of the catheter assembly 100 as such relative rotation continues.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A catheter assembly, comprising:
   a first shaft member having a plurality of longitudinally spaced apart first ring members that are interconnected with a longitudinally extending first spine member;
   a second shaft member positioned within the first shaft member and connected to a distal end portion of the first shaft member, the second shaft member having a plurality of longitudinally spaced apart second ring members that are interconnected with a longitudinally extending second spine member, wherein the second shaft member is operable by applying an actuation force to the second shaft member only in a longitudinal direction, which moves at least portions of the first ring members longitudinally relative to each other to bend the first shaft member.

2. The catheter assembly of claim 1, wherein the first ring members are aligned with the second ring members.

3. The catheter assembly of claim 1, wherein the protrusions extend radially outward into a space defined between adjacent first ring members.

4. The catheter assembly of claim 3, wherein the second shaft member is operable to rotate relative to the first shaft member to contact the protrusions with the first ring members to space apart the first ring members.

5. The catheter assembly of claim 1, wherein the catheter assembly includes a longitudinal axis, and the first and second shaft members are coaxial with the longitudinal axis.

6. The catheter assembly of claim 1, wherein the second shaft member is configured to bend in a first direction upon application of a distally directed longitudinal force causing the first shaft member to bend in the first direction.

7. The catheter assembly of claim 6, wherein bending the second shaft member in the first direction spaces apart the second ring members, and bending the first shaft member in the first direction moves the first ring members closer together.

8. The catheter assembly of claim 6, wherein applying a proximally directed longitudinal force to the second shaft member bends the second shaft member in a second direction causing the first shaft member to bend in the second direction.

9. The catheter assembly of claim 8, wherein bending the second shaft member in the second direction moves the second ring members closer together, and bending the first shaft member in the first direction spaces apart the first ring members.

10. The catheter assembly of claim 1, wherein the first shaft member is configured as an integral single piece, and the second shaft member is configured as an integral single piece.

11. The catheter assembly of claim 1, wherein a spacing between adjacent first ring members varies around a circumference of the first shaft member when the first shaft member is in a rest state.

12. A method of bending a distal end portion of a catheter assembly, comprising:
   providing the distal end portion of the catheter assembly with a first shaft portion and a second shaft portion, the second shaft portion extending through a lumen defined by the first shaft portion, the first shaft portion including a plurality of longitudinally spaced apart first openings, the second shaft portion including a plurality of longitudinally spaced apart second openings, the first and second shaft portions being connected at the distal end of the catheter assembly at a connection point along the first shaft portion;
   pushing or pulling the second shaft portion relative to the first shaft portion to apply a longitudinally directed force to the second shaft portion to bend the first shaft portion, wherein the second shaft portion is configured to bend in a first direction upon application of a distally directed longitudinal force causing the first shaft portion to bend in the first direction.

13. The method of claim 12, wherein operating the second shaft portion includes axially advancing or axially retracting the second shaft portion to change a size or shape of the second openings and a size or shape of the first openings.

14. The method of claim 12, wherein operating the second shaft portion includes rotating the second shaft portion to move the protrusions within the first openings, wherein the first openings have a variable width around a circumference of the first shaft portion when the first shaft portion is in a rest state.

15. A catheter portion, comprising:
   a body portion having a bendable section, the body portion defining a lumen, a series of longitudinally spaced apart first openings being defined in the bendable section;
   a steering member extending through the lumen of the body portion and connected at a distal end thereof to the body portion at a connection point along the bendable section, the steering member including a series of longitudinally spaced apart second openings;
   wherein application of only an axial force to the steering member bends the steering member and bends the bendable section of the body portion, and wherein the steering member is configured to bend in a first direction upon application of a distally directed axial force causing the body portion to bend in the first direction.

16. The catheter portion of claim 15, wherein the body portion is coaxial with the steering member.

17. The catheter portion of claim 15, wherein the first openings are arranged facing in a direction opposite a direction in which the second openings are facing.

18. The catheter portion of claim 15, wherein the second openings are configured to close in a longitudinal direction and the first openings are configured to enlarge in the longitudinal direction upon application of a distally directed axial force to the steering member.

19. The catheter portion of claim 15, wherein the second openings are configured to enlarge in an longitudinal direction and the first openings are configured to close in the longitudinal direction upon application of a proximally directed axial force to the steering member.

20. The catheter portion of claim 15, wherein the first openings extend around at least half of a circumference of the body portion, and the second openings extend around at least half of a circumference of the steering member.

21. A method of bending a distal end portion of a catheter assembly, comprising:
providing the distal end portion of the catheter assembly with a first shaft portion and a second shaft portion, the second shaft portion extending through a lumen defined by the first shaft portion, the first shaft portion including a plurality of longitudinally spaced apart first openings, the second shaft portion including a plurality of longitudinally spaced apart second openings;
pushing or pulling the second shaft portion relative to the first shaft portion to apply a longitudinally directed force to the second shaft portion to bend the first shaft portion;
wherein operating the second shaft portion includes axially advancing or axially retracting the second shaft portion to change a size or shape of the second openings and a size or shape of the first openings.

22. A catheter portion, comprising:
a body portion having a bendable section, the body portion defining a lumen, a series of longitudinally spaced apart first openings being defined in the bendable section;
a steering member extending through the lumen of the body portion and connected at a distal end thereof to the body portion, the steering member including a series of longitudinally spaced apart second openings;
wherein application of only an axial force to the steering member bends the steering member and bends the bendable section of the body portion,
wherein the second openings are configured to close in a longitudinal direction and the first openings are configured to enlarge in the longitudinal direction upon application of a distally directed axial force to the steering member.

23. A catheter portion, comprising:
a body portion having a bendable section, the body portion defining a lumen, a series of longitudinally spaced apart first openings being defined in the bendable section;
a steering member extending through the lumen of the body portion and connected at a distal end thereof to the body portion, the steering member including a series of longitudinally spaced apart second openings;
wherein application of only an axial force to the steering member bends the steering member and bends the bendable section of the body portion,
wherein the second openings are configured to enlarge in an longitudinal direction and the first openings are configured to close in the longitudinal direction upon application of a proximally directed axial force to the steering member.

* * * * *